(12) United States Patent
Zhu et al.

(10) Patent No.: US 8,674,294 B2
(45) Date of Patent: Mar. 18, 2014

(54) SYSTEM OF ELECTROSPRAY ION GENERATOR

(75) Inventors: Yixin Zhu, Hangzhou (CN); Tingting Lu, Hangzhou (CN)

(73) Assignee: Zhejiang Haochuang Biotech Co., Inc., Hangzhou (CN)

( * ) Notice: Subject to any disclaimer, the term of this patent is extended or adjusted under 35 U.S.C. 154(b) by 246 days.

(21) Appl. No.: 13/111,054

(22) Filed: May 19, 2011

(65) Prior Publication Data

US 2013/0009055 A1   Jan. 10, 2013

(51) Int. Cl.
*H01J 49/16* (2006.01)

(52) U.S. Cl.
CPC ...................................... *H01J 49/16* (2013.01)
USPC ........................................................ 250/288

(58) Field of Classification Search
CPC ........................................................ H01J 49/16
USPC ........................................................ 250/288
See application file for complete search history.

(56) References Cited

U.S. PATENT DOCUMENTS

| | | |
|---|---|---|
| 4,861,988 A | 8/1989 | Henion et al. |
| 5,130,538 A * | 7/1992 | Fenn et al. ............... 250/282 |
| 5,412,208 A | 5/1995 | Covey et al. |
| 5,432,343 A | 7/1995 | Gulcicek et al. |
| 5,504,329 A | 4/1996 | Mann et al. |
| 6,753,521 B1 * | 6/2004 | Park et al. ............... 250/282 |
| 6,992,299 B2 | 1/2006 | Lee et al. |
| 8,227,750 B1 * | 7/2012 | Zhu et al. ............... 250/288 |

* cited by examiner

*Primary Examiner* — Jack Berman

(74) *Attorney, Agent, or Firm* — BainwoodHuang

(57) ABSTRACT

This invention relates to an analytical instrument field, specifically an instrument for pharmaceutical micromolecular and biological macromolecular ion generation. By this invention, through a hollow capillary emission needle and an emission needle bracket, the emission needle bracket forms a forward moving laminar flow gas surrounding the emission needles, eliminating the capillary counter-flow effect outside the capillary for liquid flowing out of the hollow capillary emission needle and pushing liquid forward; and vacuum lead-in capillary whose entrance is a specially designed arc mechanism, makes zero air flow speed in any direction, and the entrance happens to be the exit of the hollow capillary emission needle so as to ensure steady Taylor cone on the tip edge and ultimately obtains steady ion flow within a large flow range. This invention has advantages of steady ion emission and high ion transmission efficiency, and can be widely applied in the ion source preparation.

23 Claims, 7 Drawing Sheets

SYSTEM OF ELECTROSPRAY ION GENERATOR

BACKGROUND OF THE INVENTION

1. Field of the Invention

The present invention relates to an analytical instrument field, specifically an instrument for pharmaceutical micromolecular and biological macromolecular ion generation.

2. Description of the Related Art

It has been two decades since John B. Fenn, one of the laureates of Nobel Prize in Chemistry for 2002, applied Electrospray Ion (ESI) source to macromolecular mass spectrometry in the mid 1980s, but the ESI source mechanism still stays in two models: Ion Evaporation Model (IEM) and Charged Residue Model (CRM). The basic structure of ESI source has no essential difference with that in the 1990s.

The basic structure of ESI source is filling a hollow metal or glass capillary tube with liquid against the ion inlet of the mass spectrum, applying positive or negative high voltage to the liquid, wherein positive and negative ions are formed in the atmosphere, and the vacuum system of the mass-spectrograph absorbs some of ions into the mass analyzer of the mass-spectrograph.

For the ESI source, although the ionization probability is so high as to almost reach 100%, effective ions which transfer molecular ions to the MS (mass spectrum) mass detector range from 0.01% to 0.1% of the total number of ions.

To solve the aforementioned problem, many inventors discovered ESI sources of different mechanisms, in which their reference patent numbers are U.S. Pat. No. 4,861,988, U.S. Pat. No. 5,412,208, U.S. Pat. No. 5,432,343, U.S. Pat. No. 6,992,299 and U.S. Pat. No. 5,504,329. However, all of these prior inventions put the emission needle of the ESI source in the air. As the ion flow and the liquid flow are closely related, steady ion emission cannot be obtained within a large flow range of 100 nl/min-200 ul/min and there are no substantial improvements in the ion transmission efficiency by these prior arts.

SUMMARY OF THE INVENTION

An object of the invention is to overcome at least some of the drawbacks relating to the prior arts as mentioned above.

Against existing technical shortcomings, the present invention proposes a highly efficient, rationally designed, structurally simple instrument with high ionization probability and steady ion emission.

The objective of the present invention is to provide a rationally designed, structurally simple ESI source with high ionization probability and steady ion emission.

The objective of the present invention is realized by the application of the following technical scheme: It includes hollow capillary emission needle; emission needle bracket which forms a forward moving laminar flow gas surrounding the emission needle, eliminating the capillary counter-flow effect outside the capillary for liquid flowing out of the hollow capillary emission needle and pushing liquid forward; vacuum lead-in capillary whose entrance is a specially designed arc mechanism, making zero air flow speed in any direction, and the entrance happens to be the exit of the hollow capillary emission needle so as to ensure steady Taylor cone on the tip edge of emission needle and ultimately obtain steady ion flow within a large flow range.

OVERVIEW OF EMBODIMENTS

The present invention is realized by the application of the following technical scheme:

An ESI generator, which includes a hollow capillary emission needle 3, an HV terminal 4, a hollow capillary emission needle bracket 5, and its features are:

One edge of the fixed block 6 is located in the forepart cavum of the HV terminal 4, and there is a through-hole in the middle of the fixed block 6.

The connecting pipe 7 of the liquid chromatography 76 passes through the through-hole in the fixed block 6 and is fixed in the HV terminal 4, and exterior wall of the connecting pipe 7 of the liquid chromatography 76 fits tightly the interior wall of the through-hole in the fixed block 6 to ensure that air will not leak from the tightly fit location and flow in another direction.

The vacuum lead-in capillary 2 and the HV terminal 4 connect through the hollow capillary emission needle bracket 5 whose one edge is embedded into the cavum of the HV terminal 4 and whose other edge is embedded into the cavum of the vacuum lead-in capillary 2, thus forming a connection.

The middle of the hollow capillary emission needle bracket 5 is a through cavum, which fits the diameter of the forepart cavum 501 of the hollow capillary emission needle bracket 5 to the diameter of the hollow capillary emission needle 3 and prevents air from flowing in this direction but keeps it flowing in an even more spacious direction.

The diameter of the rear cavum 503 of the hollow capillary emission needle bracket 5 is more than 1.1 times the diameter of the hollow capillary emission needle 3 so that air may flow in this direction, and the forepart cavum 501 is smaller than the rear cavum 503. There are a number of side holes 502 in the side of the hollow capillary emission needle bracket 5 connecting the rear cavum 503.

The bottom 204 of the vacuum lead-in capillary cavum 201 is a curved surface, and there is an aperture between the bottom 204 and the edge 504 of the hollow capillary emission needle bracket 5 to further ensure the gap and not to form a sealed construction.

There are gas cavities 203 on the side of the vacuum lead-in capillary 2 which pass through the side holes 502 of the hollow capillary emission needle bracket 5 so as to lead in external air.

The hollow capillary emission needle 3 and the vacuum lead-in capillary 2 are on the same axis, and the point 8 of the hollow capillary emission needle 3 is above the end plane 504 of the hollow capillary emission needle bracket 5.

Preferably, the cavum of the HV terminal 4 in the aforementioned ESI generator is large at the ends and small in the middle, and the liquid chromatography connecting pipe 7 joins the hollow capillary emission needle bracket 5 at the middle section of the cavum of the HV terminal 4.

Preferably, there are auxiliary bores 202 and air holes 203 at the side of the vacuum lead-in capillary 2 of the aforementioned ESI generator, and auxiliary bores 202 and air holes 203 run through the cavum.

As a better choice, there are 1~16 auxiliary bores 202 and gas cavities 203 each in the side of the vacuum lead-in capillary 2 of the aforementioned ESI generator, and in application, 4-8 auxiliary bores 202 are generally selected for better economic benefits and technical effects.

Preferably, 1~16 side bores 502 in the side of the hollow capillary emission needle bracket 5 of the aforementioned ESI generator run through the rear cavum 503.

Preferably, the point 8 of the hollow capillary emission needle 3 in the aforementioned ESI generator goes beyond the end plane 504 of the hollow capillary emission needle bracket 5 within a range of 5 mm. This is the specific choice technique made based on technical features of the present invention, and there are certainly better effects than existing technology beyond the aforementioned 5 mm, including leveling with the end plane 504 which generates very good effects.

Preferably, gases which run through the auxiliary bores 202 and cavities 203 in the aforementioned ESI generator are nitrogen, oxygen, argon, hydrogen, air or mixture of the same gases. As a better choice, argon or air is selected from the aforementioned gases.

Preferably, the hollow capillary emission needle 3 in the aforementioned ESI generator is hollow glass capillary or hollow metal capillary. As a better choice, the outlet of the same hollow capillary emission needle 3 is needle-like hollow glass capillary or hollow metal capillary, and specific features of the present invention will highlight technical effects of the present invention.

Preferably, the vacuum lead-in capillary 2 in the aforementioned ESI generator is of metal material, glass material or ceramic material.

Preferably, the hollow capillary emission needle 3, vacuum lead-in capillary 2, liquid chromatography connecting pipe 7, HV terminal 4 and hollow capillary emission needle bracket 5 are on the same axis.

Preferably, the other edge of the vacuum lead-in capillary 2 in the aforementioned ESI generator connects the mass spectrograph 1.

Beneficial effects: Compared with the background technology of the prior arts, rational design of the present invention puts the emission needle point 8 and vacuum lead-in capillary 2 on the same axis properly, adopts new air flow design, ensures the zero gas flow at the outlet of the hollow capillary emission needle 3.

Rational design of the vacuum lead-in capillary 2 enables ion cluster 42 of fan-shaped emission to focus on the center of the vacuum lead-in capillary 2 and leads ions into the mass spectrograph 1. The present invention has advantages of steady ion emission and high ion transmission efficiency and it is a fairly ideal ESI source.

In conclusion, the key merits of the present invention comprise:

A system of an Electrospray Ion (ESI) generator including a hollow capillary emission needle 3, a HV (high-voltage) terminal 4 and a hollow capillary emission needle bracket 5 comprises the following parts, components and processes:

a) One edge of a fixed block 6 is located in the forepart of the aforementioned HV terminal cavum and there is a through-hole in the middle of the aforementioned fixed block 6, b) A connecting pipe 7 of a liquid chromatography 72 passes through the aforementioned through-hole in the aforementioned fixed block 6 and is fixed in the aforementioned HV terminal 4, and exterior wall of the aforementioned connecting pipe 7 of the aforementioned liquid chromatography 72 fits tightly the interior wall of the aforementioned through-hole in the aforementioned fixed block 6, c) A vacuum lead-in capillary 2 and the aforementioned HV terminal 4 connect through the aforementioned hollow capillary emission needle bracket 5 whose one edge is embedded into the aforementioned HV terminal cavum and whose other edge is embedded into the aforementioned vacuum lead-in capillary cavum 201, thus to form a connection, d) The middle of the aforementioned hollow capillary emission needle bracket 5 is a through cavum which fits the forepart cavum 501 diameter of the aforementioned hollow capillary emission needle bracket 5 and a hollow capillary emission needle 3 diameter, while the rear cavum 503 diameter of the aforementioned hollow capillary emission needle bracket 5 is more than 1.1 times of the aforementioned hollow capillary emission needle 3 diameter, and the aforementioned forepart cavum 501 is less than the aforementioned rear cavum 503, wherein there are a number of side holes 502 in the side of the aforementioned hollow capillary emission needle bracket 5 connecting the aforementioned rear cavum 503, e) The bottom 204 of the aforementioned vacuum lead-in capillary cavum 201 is a curved surface, and there is an aperture between the bottom and the edge of the aforementioned hollow capillary emission needle bracket 5, wherein there are gas cavities 203 on the side of the aforementioned vacuum lead-in capillary 2 passing through the side hole 502 of the aforementioned hollow capillary emission needle bracket 5, and f) The aforementioned hollow capillary emission needle 3 and the aforementioned vacuum lead-in capillary 2 are on the same axis, and the aforementioned hollow capillary emission needle point 8 is above the end plane 504 of the aforementioned hollow capillary emission needle bracket 5.

The aforementioned cavum of the HV terminal 4 is large at the ends and small in the middle, and the aforementioned liquid chromatography connecting pipe 7 joins the aforementioned hollow capillary emission needle bracket 5 at the middle section of the aforementioned cavum of the HV terminal 4.

The aforementioned vacuum lead-in capillary 2 has auxiliary bores 202 and gas cavities 203, and the aforementioned auxiliary bores 202 and the aforementioned gas cavities 203 are through-connected with the aforementioned cavum.

There are 1~16 auxiliary bores 202 and gas cavities 203, as set forth above, each in the side of the aforementioned vacuum lead-in capillary 2.

The aforementioned 1~16 side bores 502 in the side of the aforementioned hollow capillary emission needle bracket 5 run through the aforementioned rear cavum 503.

The aforementioned hollow capillary emission needle point 8 goes beyond the end plane of the aforementioned hollow capillary emission needle bracket 5 within a range of 5 mm. The aforementioned gases which run through the aforementioned auxiliary bores 202 and the aforementioned gas cavities 203 are nitrogen, oxygen, argon, hydrogen, air or mixture of the aforementioned gases.

The aforementioned hollow capillary emission needle 3 is hollow glass capillary or hollow metal capillary.

The outlet of the aforementioned hollow capillary emission needle 3 is needle-like hollow glass capillary or hollow metal capillary.

The aforementioned vacuum lead-in capillary 2 is of metal material, glass material or ceramic material.

The aforementioned hollow capillary emission needle 3, the aforementioned vacuum lead-in capillary 2, the aforementioned liquid chromatography connecting pipe 7, the aforementioned HV terminal 4 and the aforementioned hollow capillary emission needle bracket 5 are on the same axis.

The aforementioned other edge of the aforementioned vacuum lead-in capillary 2 connects a mass spectrograph 1.

All these and other introductions of the present invention will become much clear when the drawings as well as the detailed descriptions are taken into consideration.

BRIEF DESCRIPTION OF THE DRAWINGS

For the full understanding of the nature of the present invention, reference should be made to the following detailed descriptions with the accompanying drawings in which:

FIG. 8 is the test data diagram II.

Like reference numerals refer to like parts throughout the several views of the drawings.

DESCRIPTION OF THE PREFERRED EMBODIMENT

Figure 1:
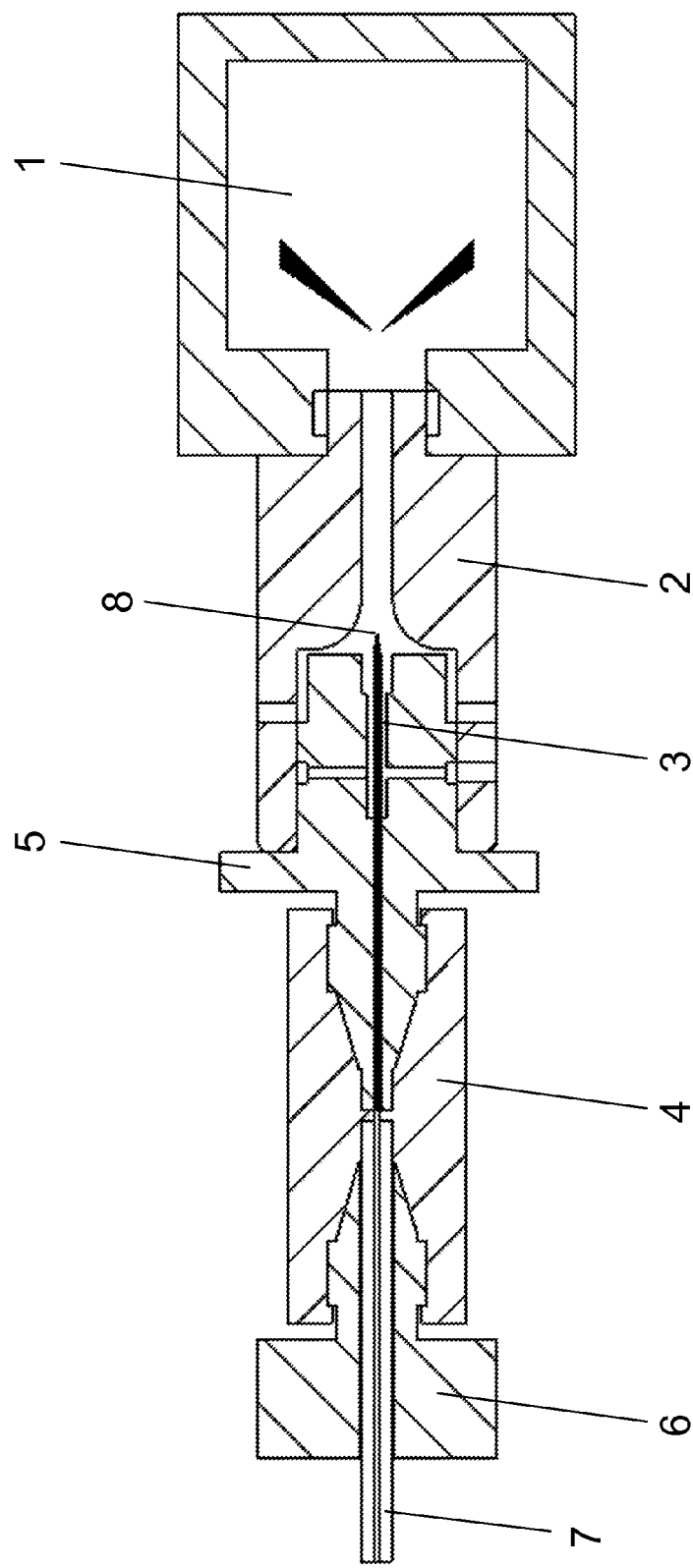
FIG. 1 is the section view diagram of an example ion source.
Figure 2:
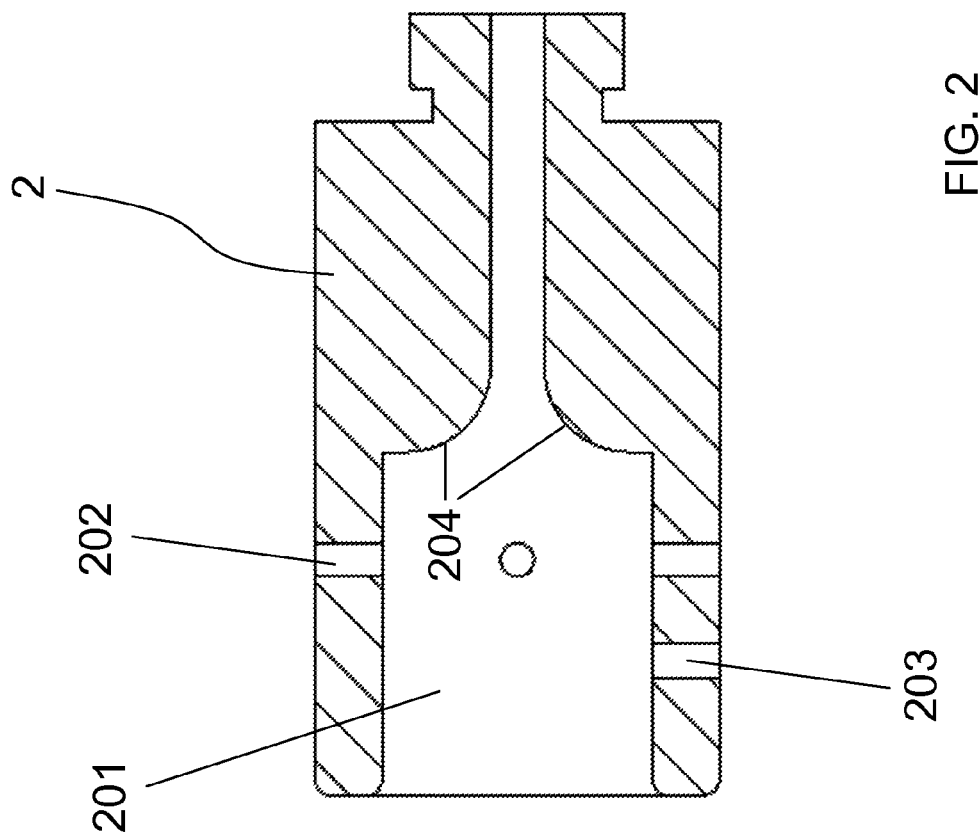
FIG. 2 is the structural schematic diagram of the vacuum lead-in capillary of the ion source.

The present invention will be described more fully hereinafter with reference to the accompanying drawings, in which some examples of the embodiments of the invention are shown. Indeed, the present invention may be embodied in many different forms and should not be construed as limitation to the embodiments set forth herein, rather, these embodiments are provided by way of example so that this disclosure will satisfy applicable legal requirements. Like numbers refer to like elements throughout.

The following specification for the implementation of the present invention is made based on the attached drawings.

Example 1

Based on the structure demonstrated by FIG. 1, FIG. 2, FIG. 4 and FIG. 5, an ESI generator 5 is made, including the hollow capillary emission needle 3, HV terminal 4, hollow capillary emission needle bracket 5, one edge of the fixed block 6 located on the cavum forepart 501 of the HV terminal 4, and there is a through-hole in the middle of the fixed block 6; liquid chromatography connecting pipe 7 runs through the through-hole in the fixed block 6 and is fixed in the HV terminal 4, and the exterior wall of the liquid chromatography connecting pipe 7 fits well the interior wall of the through-hole of the fixed block 6; the vacuum lead-in capillary 2 connects the HV terminal 4 through the hollow capillary emission needle bracket 5 whose one edge is embedded into the cavum of the HV terminal 4 and whose other edge is embedded into the cavum 201 of the vacuum lead-in capillary 2, forming connection; the middle of the hollow capillary emission needle bracket 5 is a through cavum, the diameter at the forepart cavum 501 embedded with the HV terminal 4 matches with the diameter of hollow capillary emission needle 3; the rear cavum 503 diameter of the hollow capillary emission needle bracket 5 is more than 1.2 times the hollow capillary emission needle diameter, and there are a number of side holes 502 in the side of the hollow capillary emission needle 3 connecting the rear cavum 503; the bottom 204 of the vacuum lead-in capillary cavum 201 is a curved surface, and there is an aperture between the bottom 204 and the edge of the hollow capillary emission needle bracket 5; there are pores 203 on the side of the vacuum lead-in capillary 2 which pass through the side hole 502 of the hollow capillary emission needle bracket 5; the hollow capillary emission needle 3 and the vacuum lead-in capillary 2 are on the same axis, the hollow capillary emission needle point 8 is above the end plane 504 of the hollow capillary emission needle bracket 5; the HV terminal cavum is large at the ends and small in the middle, the liquid chromatography connecting pipe 7 joins the hollow capillary emission needle bracket 5 at the middle section of the HV terminal cavum.

Figure 6:
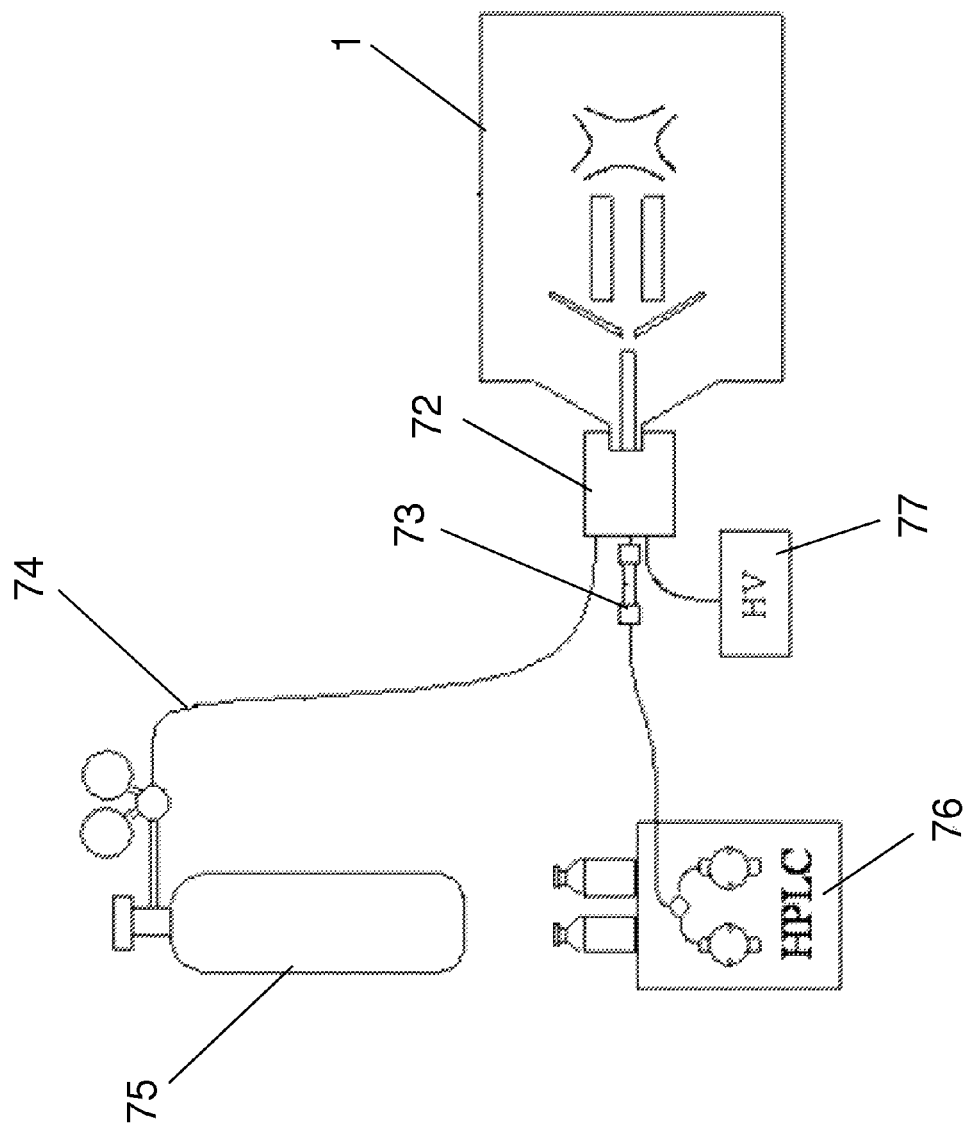
FIG. 6 is the schematic diagram for the connection of application device of the ion source.

Then, based on the structure demonstrated by FIG. 6, it connects the aforementioned ESI generator with mass spectrograph 1, gas conduit 74, liquid chromatography separation column 73, ESI source 72, liquid chromatography 76, HV power supply 77 and HV auxiliary gas cylinder 75 into a whole.

Figure 4:
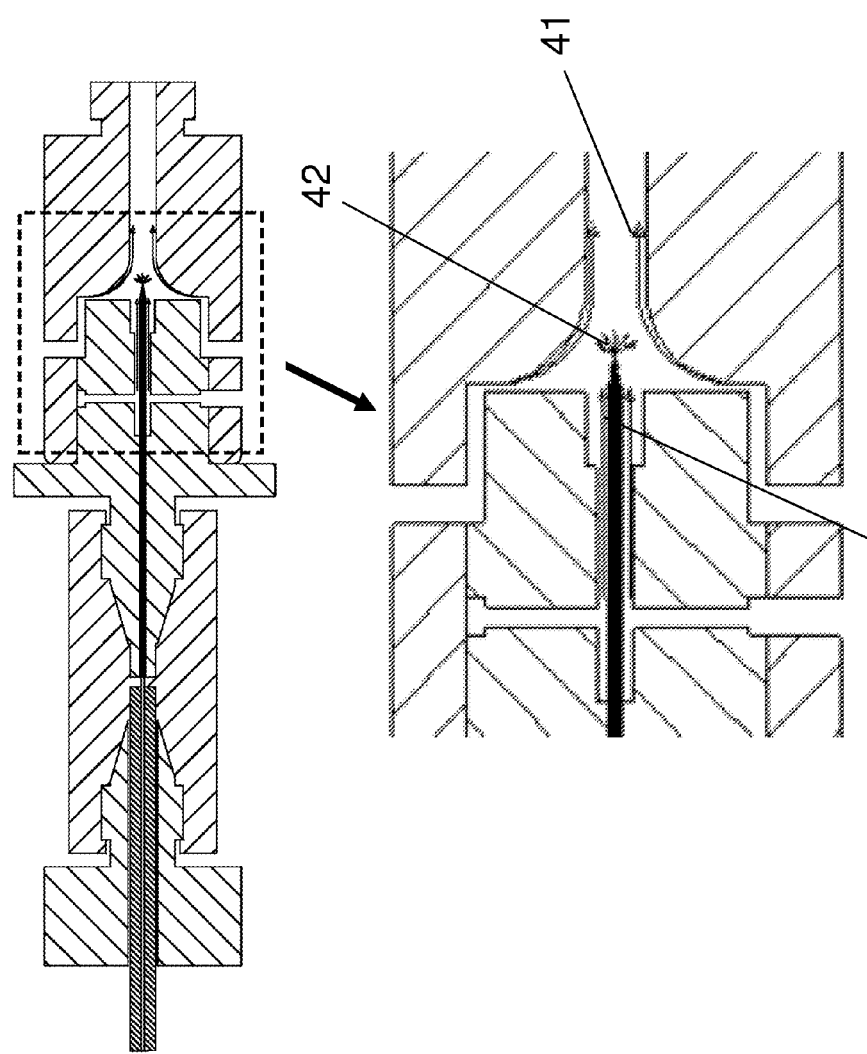
FIG. 4 is the section view diagram of application structure of the ion source.
Figure 5:
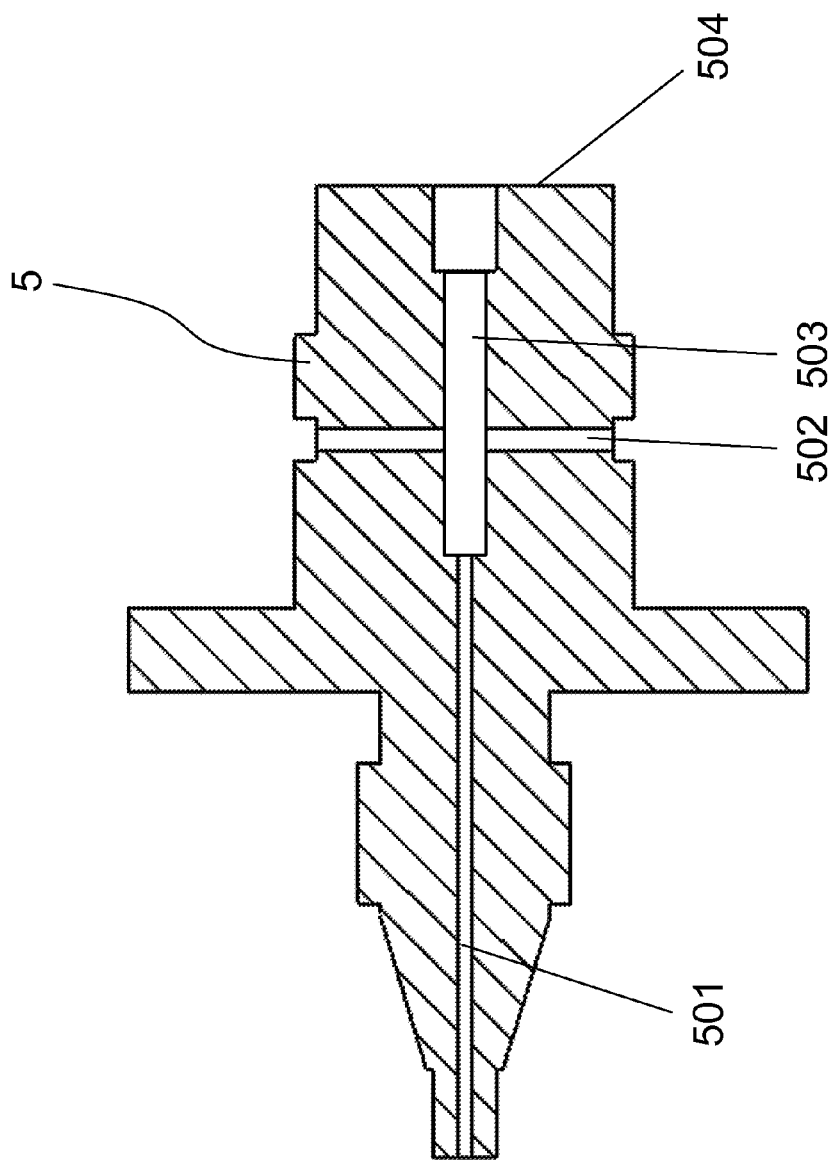
FIG. 5 is the structural schematic diagram of the hollow capillary emission needle bracket of the ion source.

The hollow capillary emission needle 3 is inserted into the vacuum lead-in capillary 2, liquid flows into the hollow capillary emission needle 3 through the liquid chromatography connecting pipe 7, the vacuum system of the mass spectrograph 1, through the vacuum lead-in capillary 2, forms an auxiliary air flow surrounding the hollow capillary emission needle 3 between the hollow capillary emission needle 3 and the hollow capillary emission needle bracket 5, as set forth above, when high voltage is applied to the HV terminal 4, and a Taylor cone is formed at the top of the hollow capillary emission needle 3, the emission fan-shaped ion cluster 42 at the top of the Taylor cone, due to the gas suction effect of the mass spectrograph 1, a rotating air flow 41 is formed on the surface of the vacuum lead-in capillary 2, and the ion focus at the vacuum lead-in capillary center is sent into the mass spectrograph 1, as shown in FIG. 4.

Figure 3:
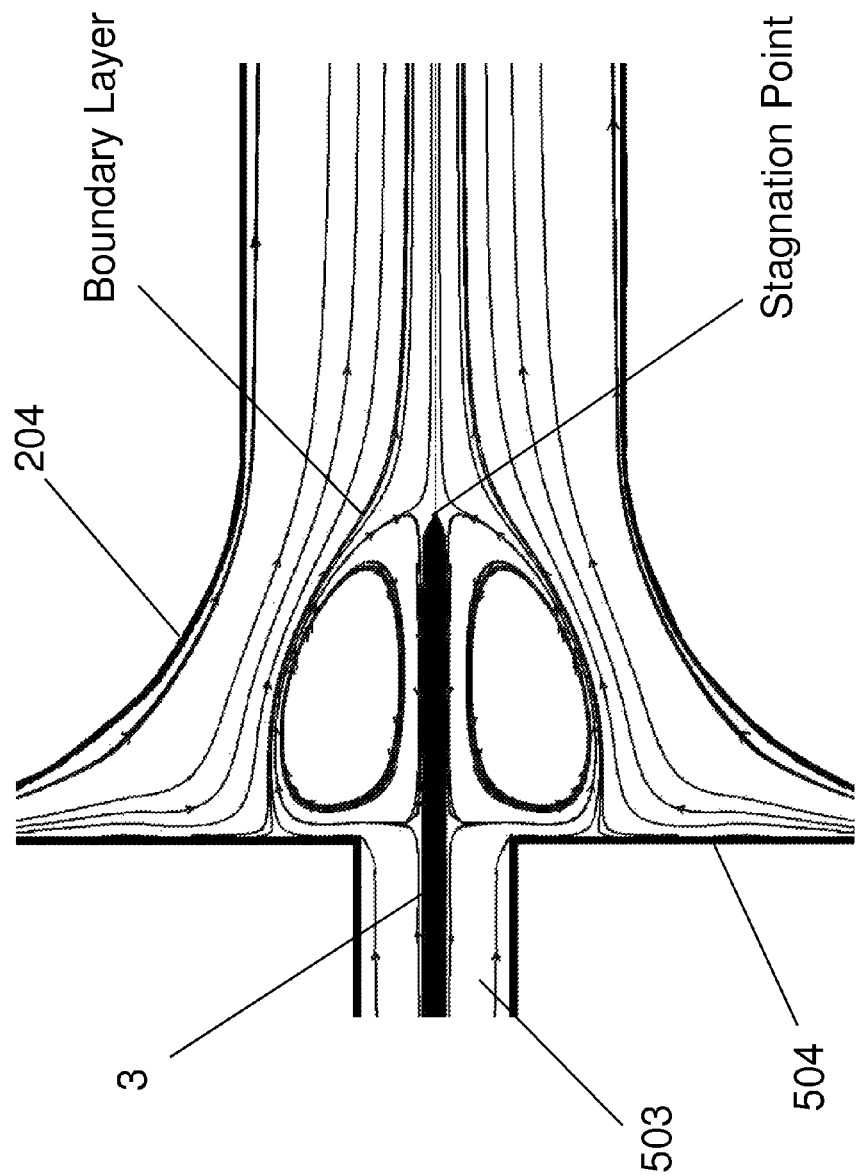
FIG. 3 is the illustrative diagram of heated capillary gas flow of the ion source.

FIG. 3 is the illustrative diagram of the implementation of the present invention. Liquid chromatograph flow is 50 ml/min, sample size is 100 femtomoles, and femtomole is a measuring unit, sample is Sigma's Angiotensin III, mass spectrum is Thermo LCQ ion well. Data in FIG. 7 was obtained from tests.

Figure 7:
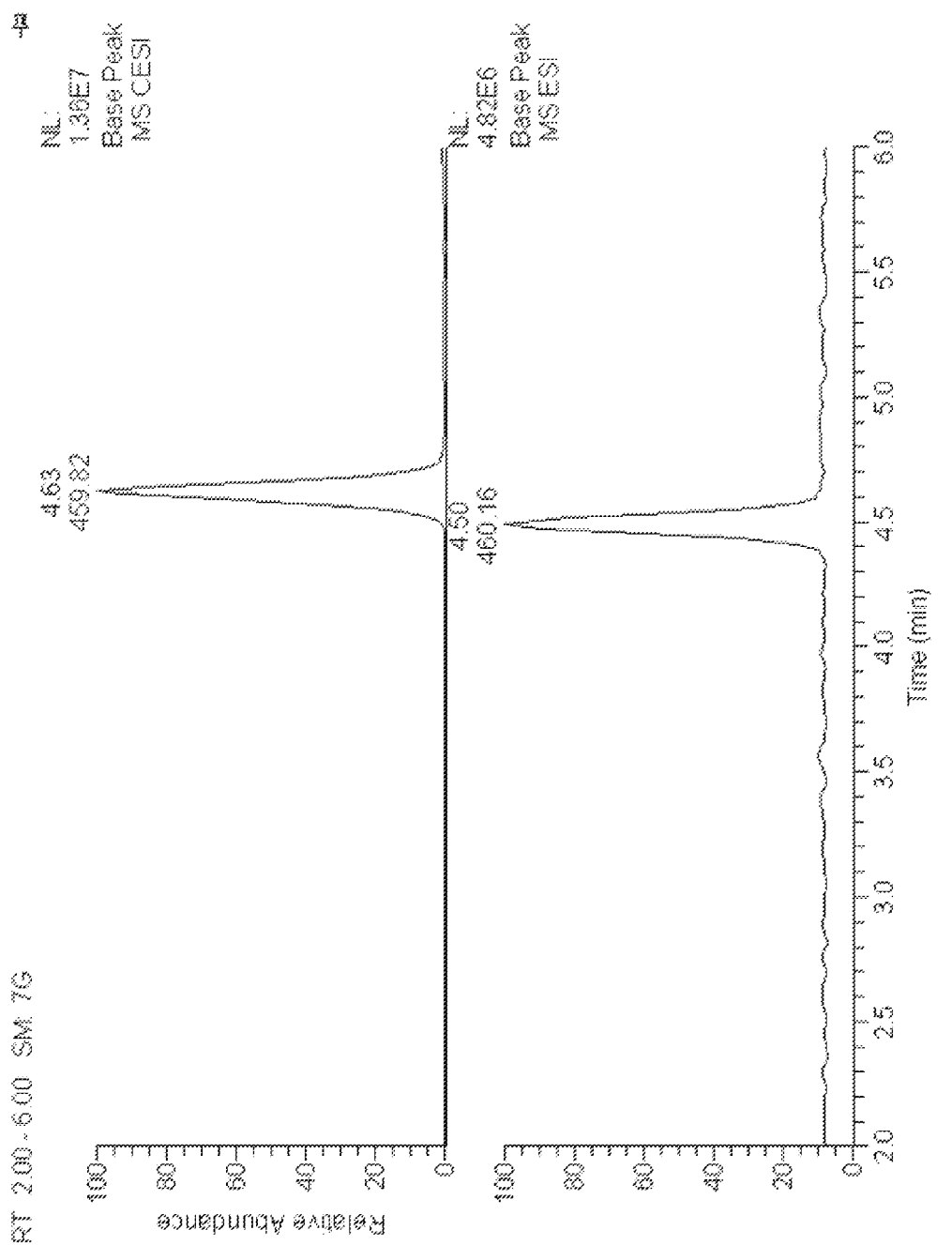
FIG. 7 is the test data diagram I.

FIG. 7 shows the present invention's result at its upper part and the conventional ESI source result at the lower part. The figure shows the signal intensity increases twice, and the SNR (signal noise rate) is around 30 times of the conventional ESI source.

Liquid chromatograph flow is 200 nl/min, sample size is 50 femtomoles, sample is US Michrom's enzymolysis bovine albumin, mass spectrum is Thermo LCQ ion well. Data in FIG. 8 was obtained from tests.

FIG. 8 shows the total ion trajectory of mass spectrum at its upper part and the highest ion peak trajectory at the lower part. FIG. 8 shows no interruption occurs in either of the two ion trajectories during the 75-min analysis, indicating the ion flow is very stable and the conventional ESI source is completely unreachable and impossible.

Example 2

Given the same structure as in Example 1, there are auxiliary bores 202 in the side of the vacuum lead-in capillary 2, the auxiliary bores run 202 through the cavum; there are four auxiliary bores 202 in the side of the vacuum lead-in capillary 2, gas which runs through auxiliary bores 202 is nitrogen; the hollow capillary emission needle point goes beyond the end plane 504 of the hollow capillary emission bracket 5 by 2 mm; the hollow capillary emission needle 3 is hollow glass capillary; the vacuum lead-in capillary 2 is metal material, then the hollow capillary emission needle 3, the vacuum lead-in capillary 2, liquid chromatograph connection pipe, the vacuum lead-in capillary 2, the HV terminal 4 and the hollow capillary emission bracket 5 are put on the same axis; the rear cavum 503 diameter of the hollow capillary emission bracket 5 is 1.3 times the diameter of the hollow capillary emission needle 3; liquid chromatograph flow is 50 ml/min, sample size is 100 femtomoles, sample is Sigma's Angiotensin III, mass spectrum is Thermo LCQ ion well, the experiment results approach FIG. 7, with good technical effects.

Example 3

Given the same structure as in Example 1, there are auxiliary bores 202 in the side of the vacuum lead-in capillary 2, the auxiliary bores 202 run through the cavum; there are eight auxiliary bores 202 in the side of the vacuum lead-in capillary 2, gas which runs through auxiliary bores 202 is air; the hollow capillary emission needle point 8 goes beyond the end plane 504 of the hollow capillary emission bracket 5 by 5 mm; the hollow capillary emission needle 3 is hollow metal capillary; the vacuum lead-in capillary 2 is ceramic material, then the hollow capillary emission needle 3, the vacuum lead-in capillary 2, liquid chromatograph connection pipe 7, the vacuum lead-in capillary 2, the HV terminal 4 and the hollow capillary emission bracket 5 are put on the same axis; the diameter of the rear cavum 503 of the hollow capillary emission bracket 5 is 1.4 times the diameter of the hollow capillary emission needle 3; liquid chromatograph flow is 200 nl/min, sample size is 50 femtomoles, sample is US Michrom's enzymolysis bovine albumin, mass spectrum is Thermo LCQ ion well, the experiment results approach FIG. 8, with good technical effects.

When auxiliary gas applied in the present invention is mixture of the aforementioned gases, it generates the same good technical effects and results.

The system and method of the present invention are not meant to be limited to the aforementioned experiment, and the subsequent specific description utilization and explanation of certain characteristics previously recited as being characteristics of this experiment are not intended to be limited to such techniques.

Many modifications and other embodiments of the present invention set forth herein will come to mind to one ordinary skilled in the art to which the present invention pertains having the benefit of the teachings presented in the foregoing descriptions. Therefore, it is to be understood that the present invention is not to be limited to the specific examples of the embodiments disclosed and that modifications, variations, changes and other embodiments are intended to be included within the scope of the appended claims. Although specific terms are employed herein, they are used in a generic and descriptive sense only and not for purposes of limitation.

The invention claimed is:

1. A system of an Electrospray Ion (ESI) generator including a hollow capillary emission needle, a HV (high-voltage) terminal and a hollow capillary emission needle bracket, said system comprising:
 a) One edge of a fixed block located in the forepart of said HV terminal cavum and there being a through-hole in the middle of said fixed block,
 b) A connecting pipe of a liquid chromatography passing through said through-hole in said fixed block and fixed in said HV terminal, and exterior wall of said connecting pipe of said liquid chromatography fitting tightly the interior wall of said through-hole in said fixed block,
 c) A vacuum lead-in capillary and said HV terminal connecting through said hollow capillary emission needle bracket whose one edge being embedded into said HV terminal cavum and whose other edge being embedded into said vacuum lead-in capillary cavum, thus to form a connection,
 d) The middle of said hollow capillary emission needle bracket being a through cavum which fits the forepart cavum diameter of said hollow capillary emission needle bracket and a hollow capillary emission needle diameter, while the rear cavum diameter of said hollow capillary emission needle bracket being more than 1.1 times of said hollow capillary emission needle diameter, and said forepart cavum less than said rear cavum, wherein there existing a number of side holes in the side of said hollow capillary emission needle bracket connecting said rear cavum,
 e) The bottom of said vacuum lead-in capillary cavum being a curved surface, and there being an aperture between the bottom and the edge of said hollow capillary emission needle bracket, wherein there existing gas cavities on the side of said vacuum lead-in capillary passing through the side hole of said hollow capillary emission needle bracket, and
 f) Said hollow capillary emission needle and said vacuum lead-in capillary being on the same axis, and said hollow capillary emission needle point being above the end plane of said hollow capillary emission needle bracket.

2. A system as recited in claim 1, wherein said HV terminal cavum is large at the ends and small in the middle, and said liquid chromatography connecting pipe joins said hollow capillary emission needle bracket at the middle section of said HV terminal cavum.

3. A system as recited in claim 1, wherein said vacuum lead-in capillary has auxiliary bores and gas cavities, and said auxiliary bores and said gas cavities are through-connected with said cavum.

4. A system as recited in claim 3, wherein there are 1~16 said auxiliary bores and said gas cavities each in the side of said vacuum lead-in capillary.

5. A system as recited in claim 4, wherein said 1~16 side bores in the side of said hollow capillary emission needle bracket run through said rear cavum.

6. A system as recited in claim 1, wherein said hollow capillary emission needle point goes beyond the end plane of said hollow capillary emission needle bracket within a range of 5 mm.

7. A system as recited in claim 1, wherein said gases which run through said auxiliary bores and said gas cavities are nitrogen, oxygen, argon, hydrogen, air or mixture of said gases.

8. A system as recited in claim 7, wherein said gases which run through said auxiliary bores and said gas cavities are nitrogen or air.

9. A system as recited in claim 1, wherein said hollow capillary emission needle is hollow glass capillary or hollow metal capillary.

10. A system as recited in claim 9, wherein the outlet of said hollow capillary emission needle is needle-like hollow glass capillary or hollow metal capillary.

11. A system as recited in claim 1, wherein said vacuum lead-in capillary is of metal material, glass material or ceramic material.

12. A system as recited in claim 1, wherein said hollow capillary emission needle, said vacuum lead-in capillary, said liquid chromatography connecting pipe, said HV terminal and said hollow capillary emission needle bracket are on the same axis.

13. A system as recited in claim 1, wherein said other edge of said vacuum lead-in capillary connects a mass spectrograph.

14. An electrospray ion (ESI) generator, comprising:
 a hollow capillary emission needle bracket having a through cavum extending to an end plane and including at least one side hole extending into the through cavum for providing a first airflow path through the side hole(s) and the through cavum and toward the end plane;

a hollow capillary emission needle passing through the through cavum of the hollow capillary emission needle bracket and having a point that extends beyond the end plane of the hollow capillary emission needle bracket; and a vacuum lead-in capillary held in axial alignment with the through-cavum of the hollow capillary emission needle bracket, the vacuum lead-in capillary having (i) a curved entrance that faces the end plane of the hollow capillary emission needle bracket and (ii) multiple lateral auxiliary bores for providing a second airflow path through the lateral auxiliary bores and toward the curved entrance, wherein the first airflow path and the second airflow path meet in the vicinity of the curved entrance of the vacuum lead-in capillary.

15. The ESI generator of claim 14,
wherein the through cavum of the hollow capillary emission needle bracket has a first portion having a first diameter and a second portion having a second diameter, the second portion being closer to the end plane than the first portion, the first diameter substantially matching a diameter of the hollow capillary emission needle and the second diameter being at least 1.1 times as large as the diameter of the hollow capillary emission needle, and wherein the side hole(s) of the hollow capillary emission needle bracket open into the second portion of the through cavum of the hollow capillary emission needle bracket.

16. The ESI generator of claim 15, wherein the point of the hollow capillary emission needle extends beyond the end plane by no greater than 5 mm.

17. The ESI generator of claim 16, wherein the vacuum lead-in capillary has a vacuum lead-in capillary cavum within which an end of the hollow capillary emission needle bracket is inserted, and wherein the vacuum lead-in capillary cavum includes a set of lateral gas cavities for providing airflow for the first airflow path and a set of lateral auxiliary bores for providing airflow for the second airflow path.

18. A method of generating an ion spray for provision to a mass spectrograph, comprising:
emitting liquid from a hollow capillary emission needle extending through a through-cavum of a hollow capillary emission needle bracket;

conducting air or other gas through a first airflow path along at least a portion of the through cavum parallel to the hollow capillary emission needle and toward a vacuum lead-in capillary coupled to the hollow capillary emission needle bracket;

conducting air or other gas through a second airflow path through at least one lateral opening formed at a junction of the hollow capillary emission needle bracket and the vacuum lead-in capillary; and combining the air or other gas conducted through the first airflow path with the air or other gas conducted through the second airflow path near a curved entrance of the vacuum lead-in capillary.

19. The method of claim 18, wherein combining the air or other gas from the first and second airflow paths includes generating a region of substantially zero airflow speed in any direction at the curved entrance of the vacuum lead-in capillary.

20. The method of claim 19, wherein combining the air or other gas from the first and second airflow paths includes generating a laminar flow of air or other gas through the vacuum lead-in capillary.

21. The method of claim 18, further comprising supplying hydrogen gas as the gas conducted through the first airflow path and the second airflow path.

22. The method of claim 18, further comprising supplying nitrogen gas as the gas conducted through the first airflow path and the second airflow path.

23. The method of claim 18, further comprising supplying a mixture of gases, including any of nitrogen, oxygen, argon, hydrogen, and/or air, as the gas conducted through the first airflow path and the second airflow path.

* * * * *